United States Patent [19]

Schulz et al.

[11] 4,127,455
[45] Nov. 28, 1978

[54] MANUFACTURE OF SYMMETRICAL CAROTENOIDS

[75] Inventors: Bernhard Schulz, Schwetzingen; Hans Grassner, Heidelberg; Peter Jaeger, Ludwigshafen; Heinz Nohe, Meckenheim, all of Fed. Rep. of Germany

[73] Assignee: BASF Aktiengesellschaft, Ludwigshafen am Rhein, Fed. Rep. of Germany

[21] Appl. No.: 817,252

[22] Filed: Jul. 20, 1977

[30] Foreign Application Priority Data

Aug. 9, 1976 [DE] Fed. Rep. of Germany ....... 2635802

[51] Int. Cl.² .................. C25B 3/02; C07C 11/21
[52] U.S. Cl. ........................................ 204/78; 204/72; 260/666 C
[58] Field of Search ................... 204/72, 78, 59 R

[56] References Cited

U.S. PATENT DOCUMENTS

| 3,480,525 | 11/1969 | Wessling et al. | 204/59 R |
| 3,480,527 | 11/1969 | Wessling et al. | 204/73 |
| 3,764,492 | 10/1973 | Baizer et al. | 204/59 R |
| 3,859,183 | 1/1975 | Wagenknecht | 204/59 R |

Primary Examiner—F.C. Edmundson
Attorney, Agent, or Firm—Keil, Thompson & Shurtleff

[57] ABSTRACT

Symmetrical carotenoids are manufactured from the molecular halves thereof by a process wherein phosphonium salts of the molecular halves of these symmetrical carotenoids are oxidized electrochemically in a solvent and in the presence of a base, causing the molecular halves to dimerize, with elimination of substituted phosphine oxide.

4 Claims, No Drawings

MANUFACTURE OF SYMMETRICAL CAROTENOIDS

The present invention relates to a process for the manufacture of symmetrical carotenoids from the phosphonium salts of the molecular halves, by electrochemical oxidation.

Numerous methods of synthesis of carotenoids, especially of β-carotene, have been disclosed. However, the conventional processes suffer from a number of disadvantages, especially as regards the yields or the accessibility of the starting materials. In addition, the reaction conditions entail expense, since it is necessary to exclude water and oxygen or to maintain low temperatures.

German Pat. No. 1,068,709 discloses a process for the manufacture of β-carotene by the $C_{20} + C_{20}$ principle of synthesis, from axerophthylphosphonium salt and vitamin A-aldehyde in a Wittig reaction in a substantially anhydrous solvent under a stream of nitrogen, with exclusion of atmospheric oxygen. One of the disadvantages of this process is that vitamin A-aldehyde, which is chemically very sensitive and not easily manufactured industrially, is used as the starting material.

In Chemische Berichte 96 (1963), 1,899 et seq., H. J. Bestman and O. Kratzer disclose that phosphine-alkylenes, which are manufactured from the phosphonium salts under the conditions of a Wittig reaction, can be dimerized by treatment with oxygen, resulting in elimination of triphenylphosphine oxide and formation of a double bond. The use of this reaction to manufacture β-carotene from triphenylphosphine-axerophthylene is disclosed in German Pat. No. 1,148,542 and gives only a 35% yield of crude carotene. A publication in Liebigs Annalen der Chemie, 721 (1969), 34 et seq., also confirms that when using this dimerization with oxygen or air for the manufacture of β-carotene or carotenoids, the results achieved are unsatisfactory.

D. B. Denney, in J. Org. Chem. 28 (1963), 778 et seq. discloses that acylmethylenephosphoranes can be dimerized by means of peracetic acid, with elimination of triphenylphosphine oxide and formation of a double bond. Phosphoranes which do not have a carbonyl group in the β-position to the phosphorus atom, eg. triphenylbenzylidene-phosphorane, were found by Denney not to be dimerizable with peracetic acid.

H. J. Bestmann, L. Kisielowski and W. Distler (Angew. Chem. 88 (1976), 297 et seq.) state that the oxidation of alkylidene-triphenylphosphoranes can be carried out by means of phosphite-ozone adducts in toluene or methylene chloride as the solvent. It is true that a 75% yield of β-carotene can be obtained in this way, but the reaction requires maintaining very low temperatures of from about −70° to −80° C.

We have found a process for the manufacture of symmetrical carotenoids from phosphonium salts of the molecular halves of these symmetrical carotenoids, in which the said salts are oxidized electrochemically in a solvent and in the presence of a base, causing the molecular halves to dimerize, with elimination of substituted phosphine oxide.

Anodic coupling and condensation reactions have been disclosed, for example the Kolbe reaction, which entails the coupling of two carboxylic acids, with elimination of carbon dioxide. However, the course of the Kolbe reaction greatly depends on the structure of the carboxylic acid radical. In particular, double bonds on the carbon atom in the 2-position substantially reduce the yield (B. C. L. Weedon, "Kolbe Electrolytic Synthesis" in "Advances in Organic Chemistry", volume 1, page 1 et seq., Interscience Publishers Inc., New York 1960).

It was therefore surprising that the anodic condensation of the phosphonium salts leads to the corresponding dimers with good yields under industrially easily realizable conditions.

In the case of the manufacture of β-carotene, the reaction can be schematically represented as follows:

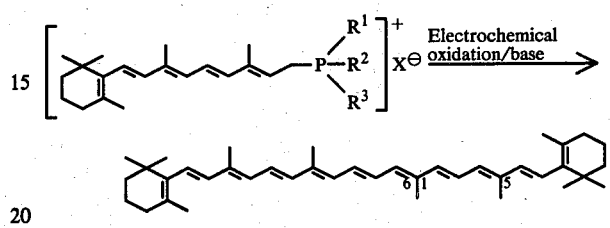

In this equation, $R^1$, $R^2$ and $R^3$ are aromatic, aliphatic or cycloaliphatic radicals, eg. phenyl, tolyl, cyclohexyl or butyl, and X is one equivalent of the radical of an inorganic or organic strong acid, eg. bisulfate, sulfate, phosphate, tetrafluoborate, acetate, toluenesulfonate and benzenesulfonate. Of course, phosphonium salts with other acid radicals as the anions, provided they are inert under the reaction conditions, can also be used. Bisulfate is the preferred anion.

Phosphonium salts to be used for the symmetrical carotenoids to be synthesized by the process of the invention are compounds with tetrasubstituted phosphorus as the cation, in which one substituent is the molecular half of the carotenoid and the remaining three substituents are the radicals $R^1$, $R^2$ and $R^3$. They may be obtained, for example, from the corresponding alcohols or esters by processes disclosed in the literature, eg. as described in German Pat. No. 1,068,709, German Pat. No. 1,158,505, German Pat. No. 1,155,126 or Houben-Weyl, volume 12/1, pages 79 et seq., Georg-Thieme-Verlag, Stuttgart, 4th edition, 1963.

The preferred phosphonium salts are substituted or unsubstituted triarylphosphonium salts, especially the triphenylphosphonium salts, tricycloaliphatic phosphonium salts, especially tricyclohexylphosphonium salts, or trialkylphosphonium salts, especially tributylphosphonium salts.

For the purposes of the present description, a substituted phosphine oxide is a phosphine oxide with the radicals $R^1$, $R^2$ and $R^3$ as substituents.

The process of the invention in particular relates to the manufacture of carotenoids of 10 to 40 carbon atoms in the isoprenoid skeleton, preferably carotenoid compounds of 20 to 40 carbon atoms. These compounds are distinguished by a plurality of conjugated double bonds. As a rule, from 3 to 11, preferably from 7 to 11, double bonds are present; two of these may also be triple bonds.

For the purposes of the invention, symmetrical carotenoids are, for example, hydrocarbons (carotenes) and their oxidized derivatives (xanthophylls) which are built up of 8 isoprenoid units in such a way that the arrangement of the said units in the center of the molecule runs in opposite directions, so that the two central methyl groups are in the 1,6-position to one another and the remaining non-terminal methyl groups are in each case in the 1,5-position to the adjacent central methyl group. In the center of a carotenoid there is a chain of conjugated double bonds.

All carotenoids can be formally derived from the open-chain structure of lycopine ($C_{40}H_{56}$) by cyclizing, dehydrogenating, hydrogenating or oxidizing, or by combination of these reactions.

Examples of phosphonium salts of molecular halves are axerophthylphosphonium bisulfate for the manufacture of β-carotene, 3,7,11,15-tetramethyl-hexadeca-2,4,6,8,10,14-hexaen-1-yl-triphenylphosphonium bisulfate for the manufacture of lycopine, 5-(2',6',6'-trimethyl-cyclohex-1'-en-1'-yl)-3-methylpenta-2,4-dien-1-yl-triphenylphosphonium bisulfate for the manufacture of 1,10-bis-(2',6',6'-trimethyl-cyclohex-1'-en-1'-yl)-3,8-dimethyl-deca-1,3,5,7,9-pentaene,3,7,11,15-tetramethyl-hexadeca-2,4,6,8,10-pentaen-1-yl-triphenylphosphonium bisulfate for the manufacture of 1,2,1',2'-tetrahydrolycopine, 9-(2',6',6'-trimethyl-4'-methoxy-1'-cyclohexen-1'-yl)-3,7-dimethyl-nona-2,4,6,8-tetraen-1-yl-triphenylphosphonium bisulfate for the manufacture of zeaxanthin dimethyl ether, and 9-[2',3'-4'-trimethylphenyl-1']-3,7-dimethyl-nona-2,4,6,8-tetraen-1-yl-triphenylphosphonium bisulfate for the manufacture of renierapurpurin.

Further examples which may be mentioned are 9-[2',6',6'-tri-methyl-4'-acetoxy-cyclohex-1'-en-1'-yl]-3,7-dimethyl-nona-2,4,6,8-tetraen-1-yl-triphenylphosphonium bisulfate for the manufacture of zeaxanthin diacetate, which after elimination of the acetyl groups gives zeaxanthin, 9-[2',6',6'-trimethyl-3'-acetoxy-cyclohex-1'-en-1'-yl]-3,7-dimethyl-nona-2,4,6,8-tetraen-1-yl-triphenyl-phosphonium bisulfate for the manufacture of isozeaxanthin diacetate, which after elimination of the acetyl groups gives isozeaxanthin, and 9-[2',6',6'-trimethyl-cyclohex-1'-en-3'-on-1'-yl]-3,7-dimethyl-nona-2,4,6,8-tetraen-1-yl-triphenylphosphonium bi-sulfate for the manufacture of canthaxanthin.

The process conditions substantially correspond to those conventionally used for anodic oxidations.

Suitable anode materials are those conventionally used, for example the platinum metals, graphite, gold, activated titanium, rhodium-plated titanium, platinum-plated titanium, platinum-plated tantalum and alloys of gold, for example with silver and with copper. The use of a platinum metal, in the form of a sheet, gauze, expanded metal, rod or tube is preferred. Platinum itself is the particularly preferred anode material.

The conventional materials, for example metals or graphite, may be used as the cathode.

It is advantageous to use a diaphragm to separate the cathode chamber from the anode chamber, in order to achieve good material yields and current efficiencies and trouble-free sustained operation under moderate cell voltages. The diaphragm may consist of a porous layer of clay, a porous membrane or an ion exchange membrane.

The current throughput is in general at least 2 F (corresponding to 2.96494 A.s) per mole of phosphonium salt but may normally be up to 6 times this amount. Even a greater excess does not interfere with the course of the reaction.

The current density used to carry out the reaction may vary within a wide range and is from about 1 to 500 A/dm$^2$, a density of from 5 to 300 A/dm$^2$ being preferred. A current density of 100 A/dm$^2$ is particularly preferred.

The upper temperature limit for the oxidation process is about 60° C. and the lower limit about −20° C. The use of temperatures from 0° to 30° C. is preferred.

The solvent used may be any liquid which adequately dissolves the phosphonium salt, the base and — where one is used — an electrolyte to increase the conductivity, and which is sufficiently stable under the anodic oxidation conditions. Examples are water or mixtures of water and a monohydric or polyhydric lower alcohol, ethers, hydrocarbons or chlorohydrocarbons with a relatively high water content. Depending on the solubility of the organic components in water, these mixtures may comprise two phases. Examples of organic solvent components are methanol, ethanol, propanol, isopropanol, isobutanol, glycol, glycerol, dioxane, ethylene glycol dimethyl ether, diethylene glycol diethyl ether, triethylene glycol dimethyl ether, petroleum ether, hexane, heptane, cyclohexane, methylene chloride, chloroform and carbon tetrachloride. Examples of two-phase solvent mixtures are, in particular, heptane/water, methylene chloride/water and chloroform/water. Water is the preferred solvent.

The bases used as proton acceptors are advantageously alkali metal carbonates, eg. sodium carbonate and potassium carbonate, ammonium carbonate, ammonia, alkali metal hydroxides and alkaline earth metal hydroxides, eg. sodium hydroxide, potassium hydroxide and barium hydroxide, and alkali metal alcoholates, such as sodium methylate, potassium methylate, sodium ethylate and potassium ethylate.

In general, the amount of base used is at least equivalent to the phosphonium salt but may be up to a 50-fold excess. Even a larger excess of base generally does not interfere with the course of the reaction.

If water or aqueous solvent mixtures are used, the preferred bases are sodium carbonate and potassium carbonate, which are added as solids or, advantageously, as aqueous solutions.

An electrolyte to improve the conductivity, eg. an alkali metal sulfate, phosphate or borate, may also be added to the solution to be electrolyzed.

The sequence of addition of phosphonium salt, base and electrolyte (if any), is optional. For example, the phosphonium salt solution may be subjected to the electrolysis whilst adding the calculated amount of the base over the period of the electrolysis. However, it is also possible, conversely, to electrolyze the solution of base whilst adding the phosphonium salt solution dropwise. As a further alternative, the phosphonium salt and base may be mixed before starting the electrolysis. Equally, the electrolyte solution can be electrolyzed whilst adding the phosphonium salt solution and base in the course of the electrolysis. The process may be carried out batchwise or continuously.

The dimerization reaction has as a rule ended after the electrolysis, and a precipitate of the generally sparingly soluble symmetrical carotenoid and substituted phosphine oxide forms if the process is carried out in water. To work up the mixture, the procedure generally is to filter off the precipitate, remove the phosphine oxide, for example by treatment with alcohol, and to recrystallize the symmetrical carotenoid which remains from a suitable solvent, or reprecipitate it. In some cases, recrystallization or reprecipitation of the carotenoid may even be superfluous.

If desired or required, the product can be isomerized to the all-trans form of the carotenoid in the conventional manner. For example, in the case of β-carotene such isomerization can be effected by heating a suspension of the β-carotene in aliphatic hydrocarbons, eg. heptane, or in water, for several hours.

The process of the invention for the manufacture of symmetrical carotenoids is industrially exceptionally advantageous. It was in no way to be expected that the sensitive unsaturated starting compounds and end products would not undergo any side reactions, eg. hydroxylations, formation of ketones and carboxylic acids, or polymerization, under the anodic oxidation conditions.

The particular advantage of the process, in contrast to the conversion of phosphonium salts by the Wittig reaction, is that the process can be carried out in water or aqueous solvent mixtures. The possibility of reacting the phosphonium salts in aqueous solution provides an exceptionally advantageous possibility of removing by-products which have been formed during manufacture of the phosphonium salts or were present in the starting material, by extracting the aqueous or aqueous-alcoholic solution or suspension of the phosphonium salts, prior to the electrochemical oxidation, with a water-immiscible solvent, eg. heptane. A further advantage is that the resulting carotenoid is obtained in a very pure, finely crystalline form, and in high yields, especially when the process is carried out in water.

In the process according to the invention, the final mother liquors from the vitamin A synthesis, which contain a high proportion of cis-isomers and can, in other methods, only be worked up partially and by involved and expensive processes to give all-trans-vitamin A, can also be used as the starting material for the axerophthylphosphonium salt for the manufacture of β-carotene.

The carotenoids obtained by the process of the invention may be used as pharmaceuticals, feed additives and dyes for foodstuffs and cosmetics.

EXAMPLE 1

The electrolysis cell consists of a glass cylinder of about 1 liter capacity, having a ground flange and a ground cover, the latter being provided with ground orifices to receive the current lines, cooling coil, thermometer, dropping funnel and off-gas line. A platinum gauze, acting as the cathode, is mounted in the center of the cell and is separated from the remainder of the cell by a porous hollow clay cylinder, closed at the bottom, which acts as the diaphragm. The catholyte is dilute potassium hydroxide solution. The anodes are 2 platinum gauzes each of 20 × 10 mm edge length.

A solution of 1.085 mole of potassium carbonate in 450 ml of water is introduced into the cell and electrolyzed for 6.5 hours using a current of 4 A, whilst adding a solution of 0.083 mole of axerophthyltriphenylphosphonium bisulfate in 250 ml of water. The temperature is kept at 15° C. To separate off the β-carotene completely, the mixture is stirred for a further hour and is then left to stand for about 18 hours. The precipitate is then filtered off and washed with warm water, the phosphine oxide is removed by treatment with methanol at from 50° to 60° C. and the β-carotene which remains is dissolved in methylene chloride and precipitated by means of methanol; yield, 46.1% based on phosphonium salt employed.

EXAMPLE 2

A solution of 0.083 mole of axerophthyltriphenylphosphonium bisulfate and 0.258 mole of potassium sulfate in 750 ml of water is electrolyzed, in the electrolysis cell described in Example 1, under the conditions stated in the same example. During the electrolysis, a solution of 0.723 mole of potassium carbonate in 150 ml of water is added. The yield of β-carotene is 27.5% based on phosphonium salt employed.

EXAMPLE 3

A solution of 1.085 mole of potassium carbonate and 0.1 mole of boron trioxide in 450 ml of water is electrolyzed for 6.5 hours at 7° C., using a current of 4 A, in the electrolysis cell described in Example 1. During this time, a solution of 0.045 mole of axerophthyltriphenylphosphonium bisulfate in 125 ml of water is added. After working up as described in Example 1, β-carotene is obtained in a yield of 58.2%, based on phosphonium salt employed.

EXAMPLE 4

A solution of 0.5 mole of potassium sulfate in 500 ml of water is electrolyzed for 6 hours, using a current of 3 A, in the electrolysis cell described in Example 1. During this time, a solution of 0.083 mole of axerophthyltriphenylphosphonium bisulfate in 250 ml of $H_2O$ and a solution of 0.52 mole of potassium hydroxide in 200 ml of $H_2O$ are added dropwise in such a way as not to exceed a pH of 10 over 5 hours. After working up as described in Example 1, β-carotene is obtained in a yield of 44.1%, based on phosphonium salt employed.

EXAMPLE 5

3,7,11-Trimethyl-dodeca-1,4,6,10-tetraen-3-ol is prepared, as described in German Pat. No. 1,115,238, from pseudo-ionone by a reaction with sodium acetylide in liquid ammonia followed by hydrogenation of the triple bond. Using the conventional method described in German Pat. No. 1,068,710, the product is then converted to the phosphonium bisulfate by means of triphenylphosphine and sulfuric acid. This phosphonium salt is reacted with β-formylcrotyl acetate by the method described in German Pat. No. 1,068,710 to give 1-acetoxy-3,7,11,15-tetramethyl-hexadecy-2,4,6,8,10,14-hexaene. This ester is reacted with triphenylphosphine and sulfuric acid as described in German Pat. No. 1,068,709 to give crystalline 3,7,11,15-tetramethyl-hexadeca-2,4,6,8,10,14-hexaen-1-yl-triphenylphosphonium bisulfate. Melting point 150°–155° C.

Using the method described in Example 1, a solution of 1.085 mole of potassium carbonate and 0.1 mole of boron trioxide in 450 ml of water is electrolyzed at 10° C. 0.045 mole of 3,7,11,15-tetra-methyl-hexadeca-2,4,6,8,10,14-hexaen-1-yl-triphenylphosphonium bisulfate, dissolved in 125 ml of water, is added dropwise by the method described in Example 1. After one hour, the batch is allowed to come to room temperature and is then stirred for 18 hours. Methylene chloride is added and the amount of lycopine in the methylene chloride solution is determined by UV spectrometry; the yield is 37%.

We claim:

1. A process for the manufacture of symmetrical carotenoids from substituted or unsubstituted triaryl, tricycloaliphatic or trialkylphosphonium salts of the molecular halves of said carotenoids, in which said salts are anodicly oxidized at a current density of from 1 to 500 $A/dm^2$ in water or mixtures of water and a monohydric lower alcohol, a polyhydric lower alcohol, liquid ethers, liquid hydrocarbons or liquid chlorohydrocarbons as solvent and in the presence of a proton acceptor base, causing the molecular halves to dimerize, with elimination of substituted or unsubstituted triaryl, tricycloaliphatic or trialkyl phosphine oxide.

2. A process as claimed in claim 1, in which the symmetrical carotenoids are carotenes having a hydrocarbon structure, or their oxidized derivatives, which are built up from 8 isoprenoid units in such a way that the arrangement of the isoprenoid units in the center of the molecule runs in opposite directions, so that the two central methyl groups are in the 1,6-position to one another and the remaining non-terminal methyl groups are each in the 1,5-position to the adjacent central methyl group.

3. A process as claimed in claim 1, in which an alkali metal carbonate is used as the base.

4. A process as claimed in claim 1, in which platinum is used as the anode material for the electrochemical oxidation.

* * * * *